United States Patent

Vetter et al.

Patent Number: 5,320,603
Date of Patent: Jun. 14, 1994

[54] HYPODERMIC SYRINGE FOR LYOPHILIZED MEDICAMENT

[75] Inventors: Helmut Vetter, Ravensburg; Peter Geprägs, Weingarten, both of Fed. Rep. of Germany

[73] Assignee: Arzneimitel GMBH Apotheker Vetter & Co. Ravensburg, Ravensburg, Fed. Rep. of Germany

[21] Appl. No.: 932,989

[22] Filed: Aug. 20, 1992

[30] Foreign Application Priority Data

Aug. 21, 1991 [DE] Fed. Rep. of Germany ....... 4127650

[51] Int. Cl.⁵ .................. A61M 37/00; A61M 5/32
[52] U.S. Cl. .................................... 604/82; 604/89; 604/416
[58] Field of Search ........... 604/187, 218, 191, 192, 604/232, 82, 89–92, 407, 405, 416, 199, 111, 239–243; 215/354, 356

[56] References Cited

U.S. PATENT DOCUMENTS

| | | | |
|---|---|---|---|
| 2,812,763 | 11/1957 | Ferguson | 604/199 |
| 3,070,093 | 12/1962 | Sarnoff et al. | 604/89 X |
| 3,739,779 | 6/1973 | Pfleger | 604/205 |
| 4,226,236 | 10/1980 | Genese | 604/89 |
| 4,230,231 | 10/1980 | Burnett et al. | 215/329 |
| 4,300,678 | 11/1981 | Gyure et al. | 604/111 X |
| 4,307,821 | 12/1981 | McIntosh | 222/83 |
| 4,559,052 | 12/1985 | Babson | 604/403 |
| 4,624,393 | 11/1986 | Lopez | 222/83.5 |
| 4,673,396 | 6/1987 | Urbaniak | 604/211 |
| 4,781,701 | 11/1988 | Geprägs | 604/240 |
| 4,834,149 | 5/1989 | Fournier et al. | 141/1 |
| 4,909,794 | 3/1990 | Haber et al. | 604/195 |
| 4,919,658 | 4/1990 | Badia | 604/265 |
| 5,069,323 | 4/1991 | Montgomery et al. | 215/252 |
| 5,069,670 | 12/1991 | Vetter et al. | 604/243 |
| 5,135,496 | 8/1992 | Vetter et al. | 604/111 |
| 5,139,490 | 8/1992 | Vetter et al. | 604/201 |

FOREIGN PATENT DOCUMENTS

| | | | |
|---|---|---|---|
| 0397951 | 11/1990 | European Pat. Off. | 604/240 |
| 0397977 | 11/1990 | European Pat. Off. | 604/192 |
| 1085653 | 7/1960 | Fed. Rep. of Germany | 604/192 |

*Primary Examiner*—John D. Yasko
*Assistant Examiner*—Frank Wilkens
*Attorney, Agent, or Firm*—Herbert Dubno; Andrew Wilford

[57] ABSTRACT

A hypodermic syringe has a tubular body extending along and centered on an axis and having at an axial front end a small-diameter collar formed with a front radially outwardly open seat and, axially spaced backward therefrom, a rear radially outwardly open seat. An end piece provided with a deformable plug fittable sealingly in the collar is adapted to receive a needle. Mounting fingers extending axially back from the end piece have rear ends that engage in a front position of the end piece in the front seat and in a rear position of the end piece in the rear seat. The fingers are of such an axial length that the plug is fitted snugly into the collar in the rear position but is not snugly fitted in the collar in the front position. When the end piece is in the front position a medicament in the body can be lyophilized and when in the rear position the syringe is plugged.

10 Claims, 5 Drawing Sheets

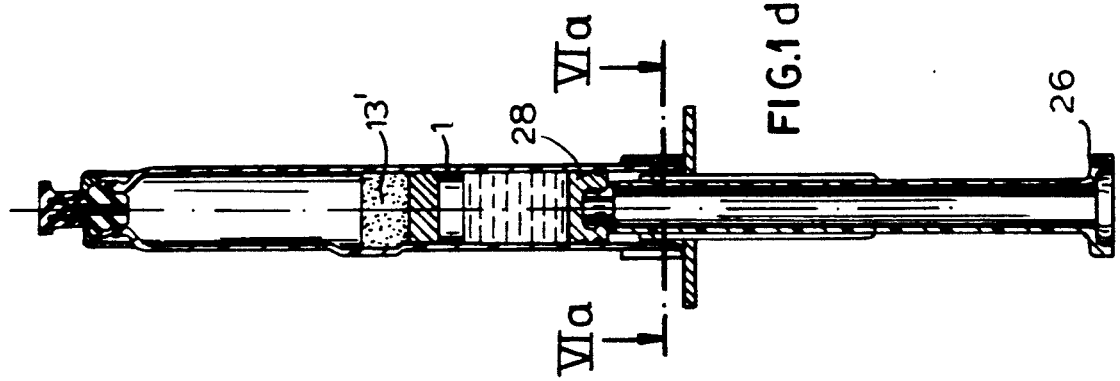
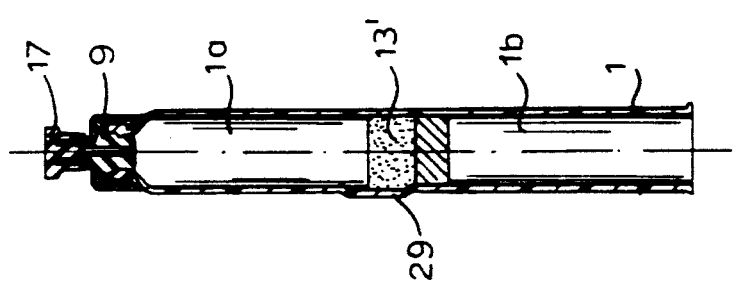
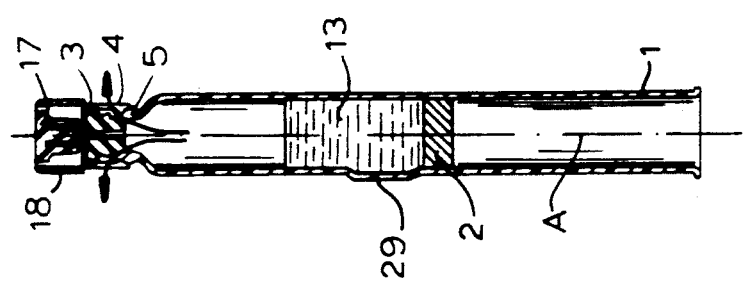
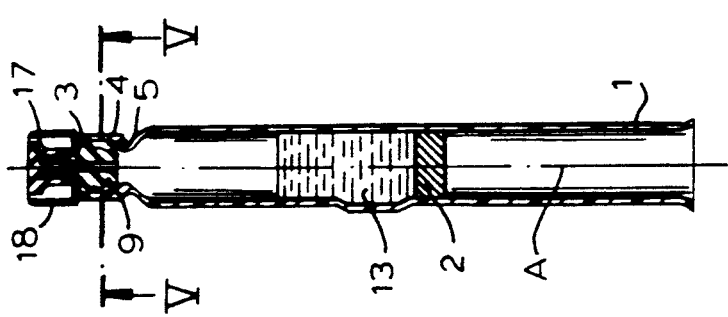

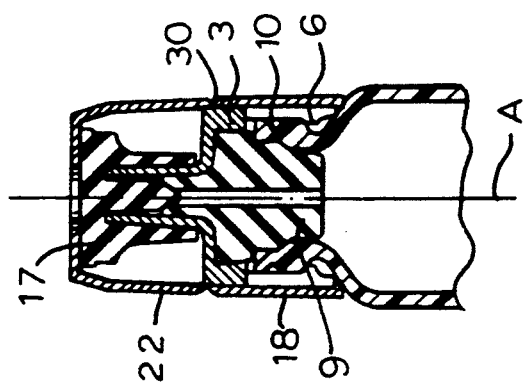
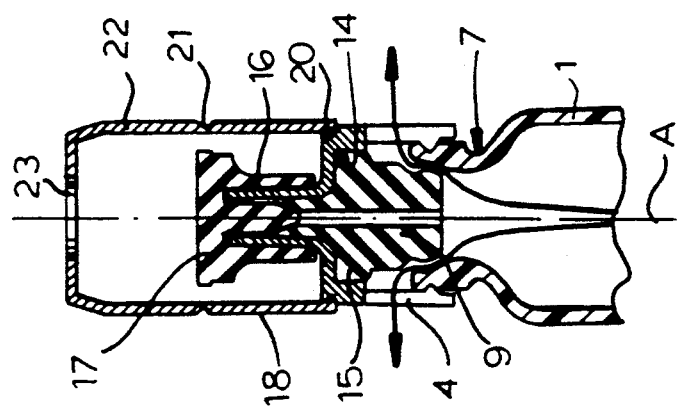
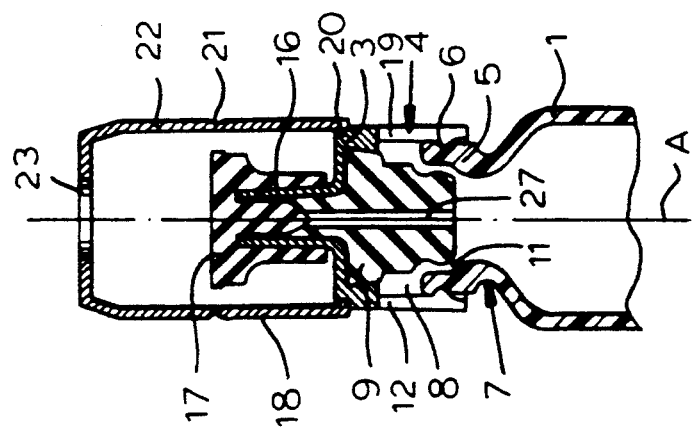

HYPODERMIC SYRINGE FOR LYOPHILIZED MEDICAMENT

FIELD OF THE INVENTION

The present invention relates to a hypodermic syringe. More particularly this invention concerns such a syringe intended to contain a lyophilized medicament.

BACKGROUND OF THE INVENTION

A standard hypodermic syringe comprises a cylindrically tubular body having a front end closed by a plug formed with a central passage extending along the axis of the body and a rear end provided with a piston longitudinally axially displaceable in the body. A quantity of liquid to be injected is held in the body between the piston and the plug and a needle is fitted to the passage at its front end so that forward displacement of the piston by a plunger forces the liquid out of the body through the needle.

A syringe for one-time use is frequently supplied already containing a lyophilized medicament, to which some solvent, for instance sterile water, is added to make the dried medicament injectable. To prepare the syringe for use a needle is mounted on the front end of the body and the liquid is drawn into it.

It is also possible as described in my U.S. Pat. No. 4,874,381 for there to be two pistons, namely a front piston that subdivides the interior of the body into a rear compartment holding the dry medicament and a front compartment holding a solvent, typically water, for it. In this case the body is formed with a bypass that permits mixing of the medicament and the liquid on axial displacement of the pistons. A rear piston is advanced to eject the contents.

In both systems the syringe is initially prepared by filling into the body a quantity of the dissolved medicament and then lyophilizing it and driving off the vaporized solvent, which escapes through the open front end of the cylinder. While maintaining sterility the front end is plugged, and the thus prepared syringe is then fitted with the necessary tip cap or the like, and is bagged.

Such an arrangement is not readily susceptible to mass production, as it is necessary to hold down costs of this throwaway item. In fact production is fairly difficult in view of the problems associated with plugging the cylinder end while maintaining the syringe and its environs sterile.

OBJECTS OF THE INVENTION

It is therefore an object of the present invention to provide an improved syringe particularly intended for distribution containing a lyophilized medicament.

Another object is the provision of such an improved syringe particularly intended for distribution containing a lyophilized medicament which overcomes the above-given disadvantages, that is which can easily be subjected to the lyophilization and subsequently sealed.

SUMMARY OF THE INVENTION

A hypodermic syringe has according to the invention a tubular body extending along and centered on an axis and having at an axial front end a small-diameter collar formed with a front radially outwardly open seat and, axially spaced backward therefrom, a rear radially outwardly open seat. An end piece provided with a deformable plug fittable sealingly in the collar is adapted to receive a needle. Mounting formations extending axially back from the end piece engage in a front position of the end piece in the front seat and in a rear position of the end piece in the rear seat. The formations are of such an axial length that the plug is fitted snugly into the collar in the rear position but is not snugly fitted in the collar in the front position.

Thus with this system it is possible to mount the end piece in place in the front position during processing, typically lyophilization, of the medicament, and then simply push it back to the rear position to hermetically seal the syringe. This is relatively easily done under sterile circumstances, making the system ideal for use for distributing prepackaged syringe doses.

According to this invention the seats are radially outwardly open grooves and the formations include a radially inwardly projecting but elastically outwardly deflectable ridge formed on a rear end of the end piece. In fact the formations are axially rearwardly extending fingers having rear ends forming the ridge and separated by notches that are radially throughgoing and axially rearwardly open. These notches afford plenty of flow cross section for devolving gases to escape from the body during lyophilization. Furthermore the end piece has a rearwardly projecting collar forming a rearwardly tapering frustoconical seat and the plug has a front end fitting complementarily in the tapering seat of the end piece. This facilitates fitting the synthetic-rubber plug in the rigid end piece. The plug itself has a rear end formed with a radially outwardly projecting annular bulge, a frustoconical intermediate surface extending from immediately forward of the bulge, and a cylindrical middle portion immediately forward of the frustoconical surface and of a diameter slightly greater than an inside diameter of the collar. This plug can hermetically seal the front end of the body.

The end piece is formed with a forwardly projecting and axially centered tubular extension and the plug has a forward extension fitting complementarily in the end-piece extension. A tip cap is normally fitted over the end-piece extension and blocks a front end of the passage.

The hypodermic syringe further has according to the invention a protector ring displaceable on the end piece between a front position mounted thereon forward of the formations and a rear position engaged around the formations and holding same in the rear position of the end piece in the rear seat against deflection therefrom. Thus when it is pushed back the protector ring prevents subsequent accidental or intentional removal of the end piece and its plug. The end cap and the protector ring are formed with a ridge and groove that radially interfit in the front position of the ring. In addition the protector ring is provided with a protector cap and is connected to it via a weakened-line region permitting the cap to be snapped off the ring. The end piece is formed with a forwardly projecting and axially centered tubular extension and the plug has a forward extension fitting complementarily in the end-piece extension. In this case the protector cap is formed with a central observation hole aligned with the tip ca but of too small a size for the tip cap to fit through. The protector cap has a front wall sitting on a front face of the tip cap in the rear position of the protector ring.

The body is formed with an axially extending and radially outwardly projecting ridge. The syringe further has according to the invention a plunger fitting over the body and having an axially extending and inwardly open groove fitting over the ridge.

BRIEF DESCRIPTION OF THE DRAWING

The above and other objects, features, and advantages will become more readily apparent from the following, reference being made to the accompanying drawing in which:

FIGS. 1a through 1d are axial sections through a syringe according to this invention in successive stages of preparation for use;

FIGS. 3a through 3c are large-scale views of details of FIGS. 1a through 1c, respectively;

FIG. 5 is a large-scale section taken along line V——V of FIG. 1a;

FIG. 6b is a section taken along line VIb——VIb of FIG. 6a.

SPECIFIC DESCRIPTION

Figure 2D:
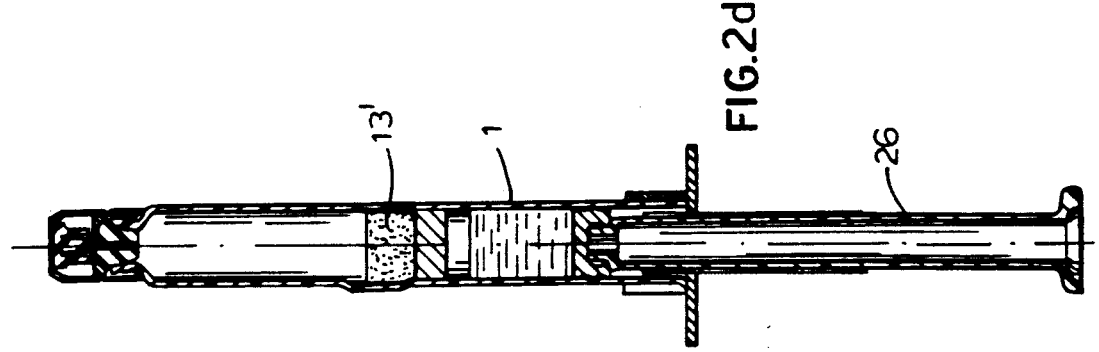
FIGS. 2a through 2d are views like FIGS. 1a through 1d of another syringe according to this invention.
Figure 2C:
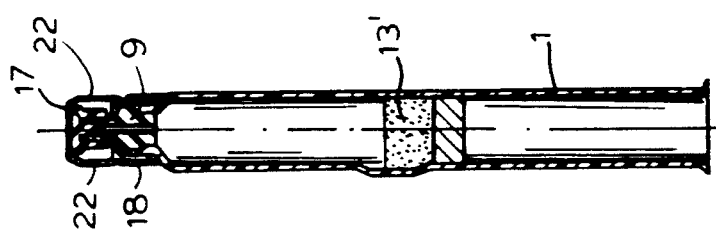
Figure 2B:
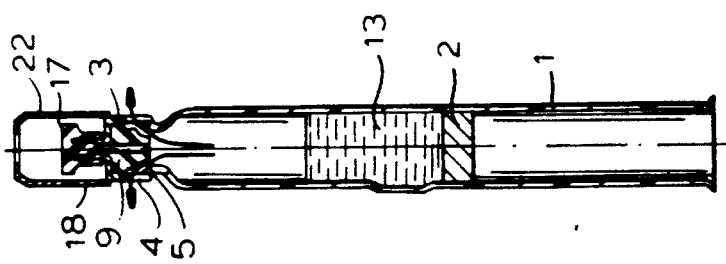
Figure 2A:
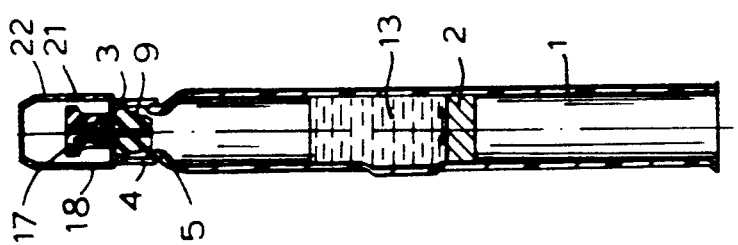

As seen in the drawing a syringe according to this invention has a basically cylindrical transparent glass or plastic body 1 centered on an axis A and having a front end formed by a small-diameter tubular collar 5 formed with a radially outwardly open front groove 10 (FIG. 3c) and a radially outwardly open rear groove 7. Normally an end piece 3 is provided with a holding skirt 4 formed with a radially inwardly projecting ridge 6 engaged to start with in the front groove 10. The body 1 is provided with an axially displaceable front piston 2 and with a rear piston 28 forming in it front and rear compartments 1a and 1b connectable through a bypass 29. A plunger 26 formed as a finger crosspiece is fitted to the rear piston 28 with a groove 25 in the plunger and an axial ridge 24 on the body 1 keeping the two from rotating relative to each other.

The end piece 3 has a rear end 14 fitted complementarily over a forwardly frustoconically flared front end 15 of an elastomeric plug 9 itself formed with a central axially through-going passage 27. The plug 3 itself has an axial rear end formed with a radially outwardly projecting ridge 9.1 joined by a rearwardly flaring frustoconical surface 9.2 to a cylindrical middle portion 9.3 of slightly greater diameter than the inner diameter of the forwardly flaring throat formed by the collar 5.

The holding skirt 4 is actually formed by an angularly equispaced array of axially rearwardly projecting fingers 19 separated by axially rearwardly open and radially throughgoing spaces or notches 12. The inner faces of the rear ends of the fingers 19 are formed with bosses that constitute the ridge 6 that sits in either of the seat grooves 7 and 10.

Figure 4C:
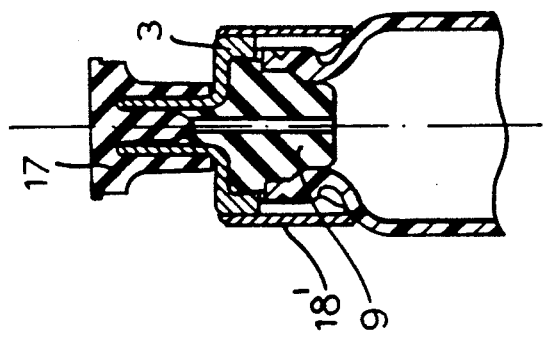
FIGS. 4a through 4c are large-scale views of details of FIGS. 2a through 2c, respectively.
Figure 4B:
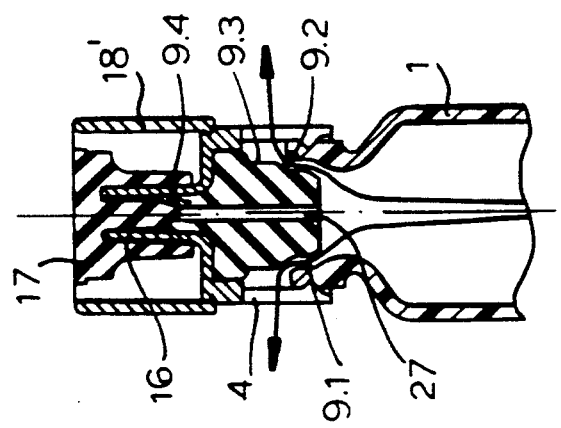
Figure 4A:
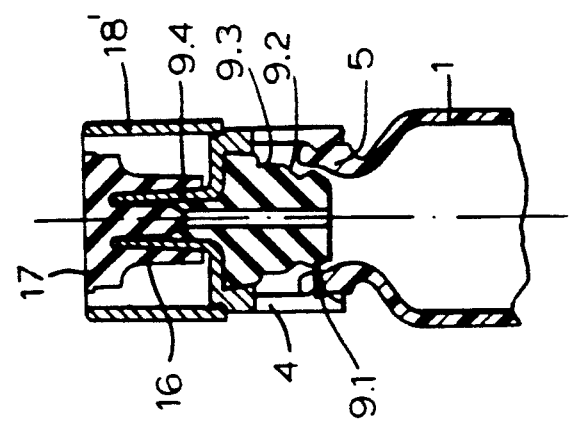
Figure 5:
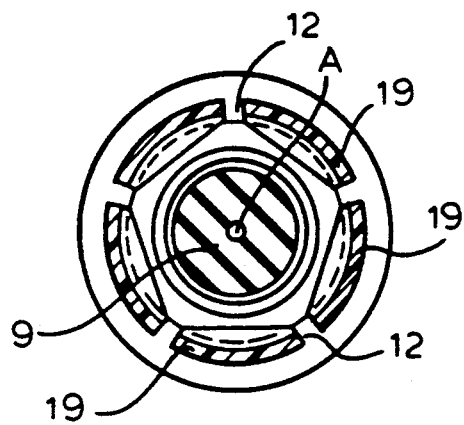
Figure 6A:
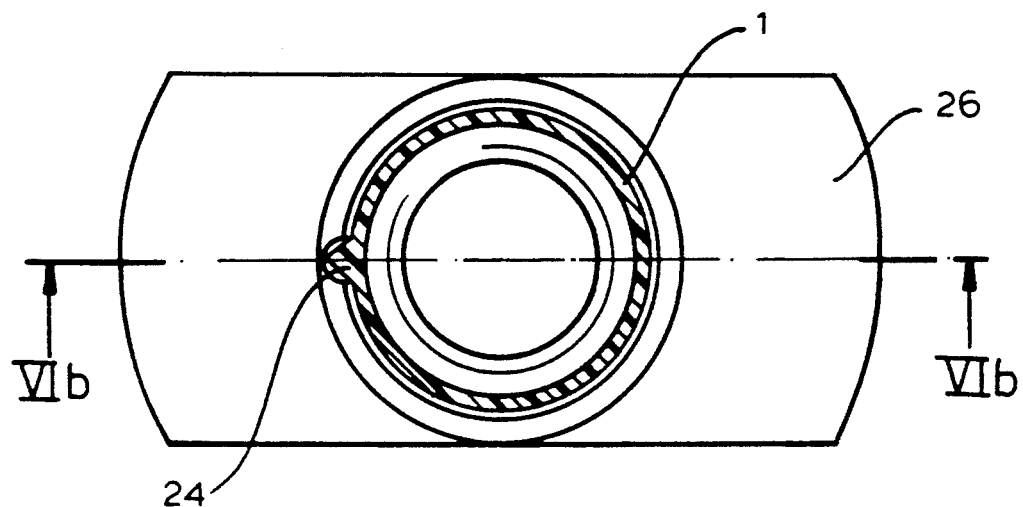
FIG. 6a is a large-scale section taken along line VIa——VIa of FIG. 1d.
Figure 6B:
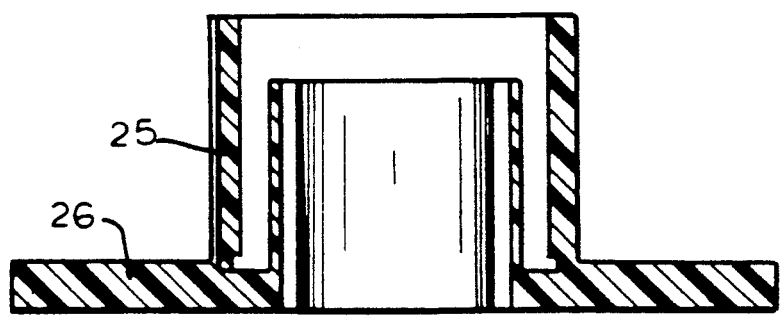

A small-diameter forward extension 16 forming the front end of the end piece 3 fits over a small-diameter forward extension 9.4 (FIG. 4a) of the plug 9, both centered on the axis A. Fitted in turn over this extension 16 is a standard tip cap 17 that engages back with a central rearward extension to seal the front end of the passage 27.

In turn a protector sleeve 18 centered on the axis A has a rear end formed with a radially inwardly projecting annular ridge 20 releasably fitted in a complementary radially outwardly open groove 30 (FIG. 3c) of the end piece 3, a front end 22 defined by a thinned-wall region 21 and formed with a central axially throughgoing hole 23. This hole 23 is of smaller diameter than the tip cap 17 and leaves its center exposed. In the arrangement of FIGS. 2a through 2d and 4a through 4c the protector 18 is a simple sleeve 18', in effect lacking everything the other protector 18 has forward of the weakened line 21.

To start with as seen in FIGS. 1a and 3a the body is positioned upright and its front compartment 1a is partially filled with a dissolved medicament 13. The end cap 3 is fitted in place in its front position with the ridge 6 engaging in the front seat groove 10. This leaves an annular gap 11 between the rear end 9.1 of the plug 9 and the inner surface of the collar 5. The protector cap 18 is fitted with its ridge 20 in the frontmost groove 30, holding it axially in front of the end piece 3 in its front position.

The liquid phase of the medicament is vaporized and escapes through the gap 11 as indicated by the arrows in FIGS. 1b and 3b, leaving behind a solid medicament 13' shown in FIGS. 1c and 3c.

Subsequently the protector cap 18 is pushed back. At first this pushes back the end piece 3 into its rear position, moving the ridge 6 of the fingers 19 from the front groove 10 to the back groove 7 and simultaneously fitting the plug 9 snugly into the collar 5. Further rearward movement slides the entire cap 18 back on the end piece into the rear position of FIG. 3c until the break line 21 lies level with the groove 30. The sleeve 18 therefore retains the fingers 19 solidly in place. The end piece 3 can as a result not move axially forward on the collar 5 since the fingers 19 cannot be deflected radially outward to disengage the ridge 6 from the groove 7. The center of the tip cap 17 is exposed at the hole 23 to make it easy to see if it has been used.

To use the syringe, the piston 26 is fitted to the piston 28. Then the front part 22 of the protector sleeve 18 is snapped off at the line 21, the tip cap 17 is taken off and discarded, and an unillustrated needle is fitted into the passage 27.

I claim:

1. A hypodermic syringe comprising:
   a tubular body extending along and centered on an axis and having at an axial front end a small-diameter collar formed with a front radially outwardly open groove and, axially spaced backward therefrom on the collar, a rear radially outwardly open groove;
   an end piece on the front end of the body;
   a deformable plug fixed on the end piece, fittable sealingly in the collar and adapted to receive a needle;
   mounting formations extending axially back from the end piece and engageable in a front position of the end piece radially inward into the front groove and in a rear position of the end piece radially inward into the rear groove, the formations being of such an axial length that
   the plug is fitted snugly into the collar in the rear position and blocks flow out of the body through the front end but
   is not snugly fitted in the collar in the front position and forms therewith an annular gap permitting flow out of the body through the front end; and
   a piston axially displaceable in the body.

2. The hypodermic syringe defined in claim 1 wherein the formations include a radially inwardly projecting but elastically outwardly deflectable ridge formed on a rear end of the formations.

3. The hypodermic syringe defined in claim 2 wherein the formations are axially rearwardly extending fingers having rear ends forming the ridge and separated by notches that are radially throughgoing and axially rearwardly open.

4. The hypodermic syringe defined in claim 1 wherein the end piece has a rearwardly projecting collar forming a rearwardly tapering frustoconical seat, the plug having a front end fitting complementarily in the tapering seat of the end piece.

5. The hypodermic syringe defined in claim 1 wherein the plug has a rear end formed with
 a radially outwardly projecting annular bulge,
 a frustoconical and rearwardly tapering intermediate surface extending from immediately forward of the bulge, and
 a cylindrical portion immediately forward of the frustoconical surface and of a diameter slightly greater than an inside diameter of the collar.

6. The hypodermic syringe defined in claim 1 wherein the end piece is formed with a forwardly projecting and axially centered tubular extension and with an axially throughgoing passage, the plug having a forward extension fitting complementarily in the end-piece extension, the syringe further comprising
 a tip cap fitted over the end-piece extension and blocking a front end of the passage.

7. The hypodermic syringe defined in claim 1, further comprising
 a protector ring axially slidable on the end piece between a front position mounted thereon forward of the formations and a rear position engaged around the formations and holding same in the rear position of the end piece in the rear groove against radial outward deflection therefrom.

8. The hypodermic syringe defined in claim 7 wherein the end piece and the protector ring are formed with a ridge and groove that radially interfit in the front position of the ring.

9. The hypodermic syringe defined in claim 7 wherein the protector ring is unitarily formed with a protector cap and is connected to it via a weakened-line region permitting the cap to be snapped off the ring.

10. The hypodermic syringe defined in claim 9 wherein the end piece is formed with a forwardly projecting and axially centered tubular extension, the plug having a forward extension fitting complementarily in the end-piece extension, the syringe further comprising
 a tip cap fitted over the end-piece extension and blocking a front end of the passage, the protector cap being formed with a central observation hole aligned with the tip cap but of too small a size for the tip cap to fit through, the protector cap having a front wall sitting on a front face of the tip cap in the rear position of the protector ring.

* * * * *